United States Patent
Bieber

(10) Patent No.: US 9,895,254 B2
(45) Date of Patent: Feb. 20, 2018

(54) LIMB SUPPORT

(71) Applicant: Edward Bieber, Bethesda, MD (US)

(72) Inventor: Edward Bieber, Bethesda, MD (US)

(73) Assignee: EDX2, LLC, Bethesda, MD (US)

(*) Notice: Subject to any disclaimer, the term of this patent is extended or adjusted under 35 U.S.C. 154(b) by 265 days.

(21) Appl. No.: 14/664,216

(22) Filed: Mar. 20, 2015

(65) Prior Publication Data

US 2015/0265453 A1  Sep. 24, 2015

Related U.S. Application Data

(60) Provisional application No. 61/955,928, filed on Mar. 20, 2014.

(51) Int. Cl.
*A61F 5/00* (2006.01)
*A61F 5/37* (2006.01)

(52) U.S. Cl.
CPC .................. *A61F 5/3738* (2013.01)

(58) Field of Classification Search
CPC .... A61F 5/3738; A61F 5/026; A61F 5/05808; A61F 5/3723; A61F 5/3746; A61F 13/041; A61F 2/78; A61F 5/0111; A61F 5/028; A61F 5/05883; A61F 5/3715; A61F 5/00; A61F 5/01; A61F 5/0118; A61F 5/013; A61F 5/04; A61F 5/05; A61F 5/05841; A61F 5/05858; A61F 5/37; A61F 5/373; A61F 5/3753; A45F 3/04; A45F 3/14; A45F 3/02; A45F 2003/142; A45F 2003/146; A45F 3/06; A45F 3/08; A45F 4/02; A45F 2003/122; A45F 2200/0566; A45F 2200/0591; A45F 3/042; A45F 3/10; A45F 5/00
USPC ............................................................. 602/4
See application file for complete search history.

(56) References Cited

U.S. PATENT DOCUMENTS

| | | | | |
|---|---|---|---|---|
| 1,304,153 | A * | 5/1919 | Bugge | A61F 5/3738 602/4 |
| 3,103,216 | A * | 9/1963 | Scott | A61F 5/3738 128/DIG. 23 |
| 4,622,961 | A * | 11/1986 | Christensen | A61F 5/3738 602/4 |
| 7,300,410 | B1 * | 11/2007 | Weber | A61F 5/37 128/878 |
| 8,523,795 | B2 * | 9/2013 | McCune | A61F 5/3738 602/4 |
| 8,845,565 | B1 * | 9/2014 | Burns | A61F 5/3738 602/4 |
| 2003/0187373 | A1 * | 10/2003 | Gaylord | A61F 5/3753 602/4 |
| 2013/0317401 | A1 * | 11/2013 | Joslin | A61F 5/3738 602/4 |

* cited by examiner

*Primary Examiner* — Victoria J Hicks
(74) *Attorney, Agent, or Firm* — Maier & Maier, PLLC

(57) ABSTRACT

A limb support device. The device may include a sling having an upper and lower section, which may be configured to hold a limb. The device may further include a support harness having a central back portion, at least one securing strap, and two support straps. The support harness may be configured to disperse the weight of the limb. The at least one securing strap and support straps may be removably connected to the sling by fasteners.

16 Claims, 3 Drawing Sheets

LIMB SUPPORT

CROSS-REFERENCE TO RELATED APPLICATIONS

This application claims priority to U.S. Provisional Patent Application No. 61/955,928 filed on Mar. 20, 2014, entitled "Limb Support." The contents of this application are incorporated by reference herein in their entirety.

BACKGROUND

Throughout the history of orthopedic medicine, there have been many different devices and methods for supporting injured limbs. Most of these supports do not distribute the weight of the limb, and sometimes a cast, very well across the user's body. For example, many arm slings do not distribute the weight equally on both shoulders. Typically these arm slings have a strap over the opposite shoulder from the injured or inoperative arm. These single strap or unequally weighted devices tend to place an unwanted pressure in a particular area of the user's body. In the example used above for arm slings, that pressure point may be against the side of the user's neck.

Additionally, many limb support devices may be difficult for a user to put on or take off due to their design having only one main clasp, buckle, or fastener.

A support device that can distribute the weight of an injured limb such that it does not cause the user discomfort may be desired. Additionally, a device that is designed to be easy for a user to apply or remove from the user's own limb or body may be desired.

SUMMARY

A limb support device may be disclosed. The device may include a sling having an upper and lower section, which may be configured to hold a limb. The device may further include a support harness having a central back portion, at least one securing strap, and two support straps. The support harness may be configured to disperse the weight of the limb. The at least one securing strap and support straps may be removably connected to the sling by fasteners.

BRIEF DESCRIPTION OF THE FIGURES

Advantages of embodiments of the present invention will be apparent from the following detailed description of the exemplary embodiments. The following detailed description should be considered in conjunction with the accompanying figures.

Exemplary

Exemplary

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1:
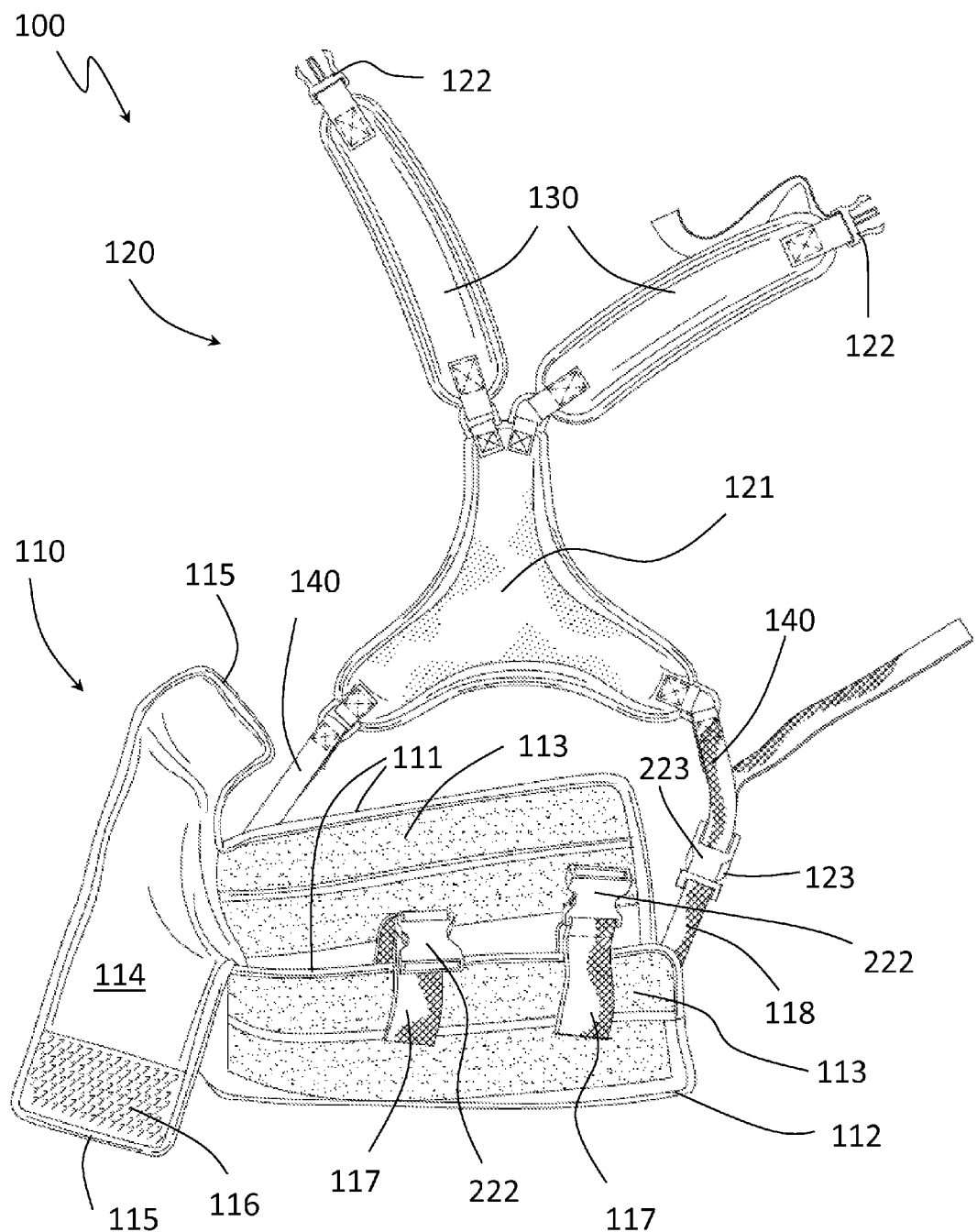
FIG. 1 shows a limb support device.
Figure 2:
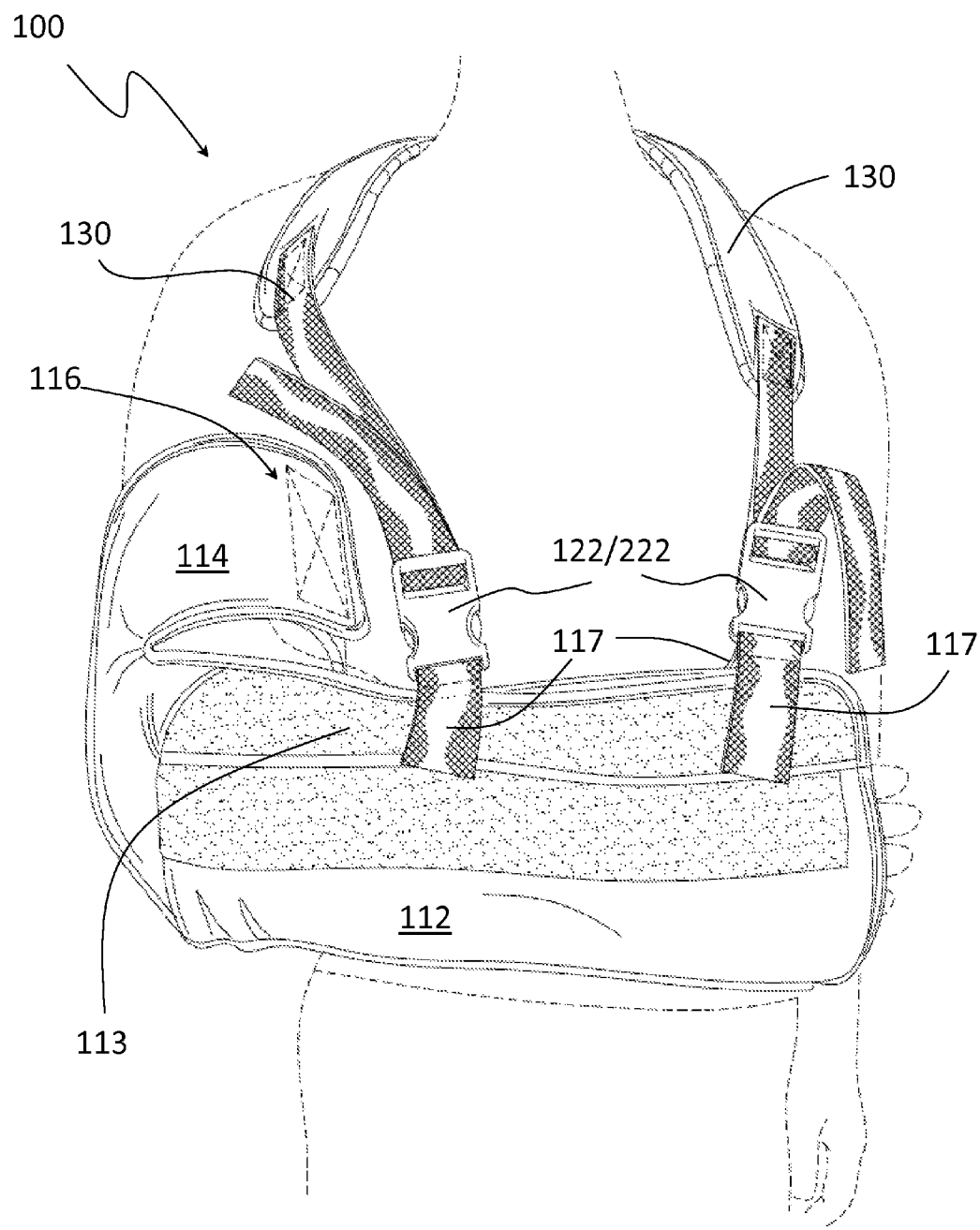
FIG. 2 shows a front perspective view of a limb support device with environment; and Exemplary
Figure 3:
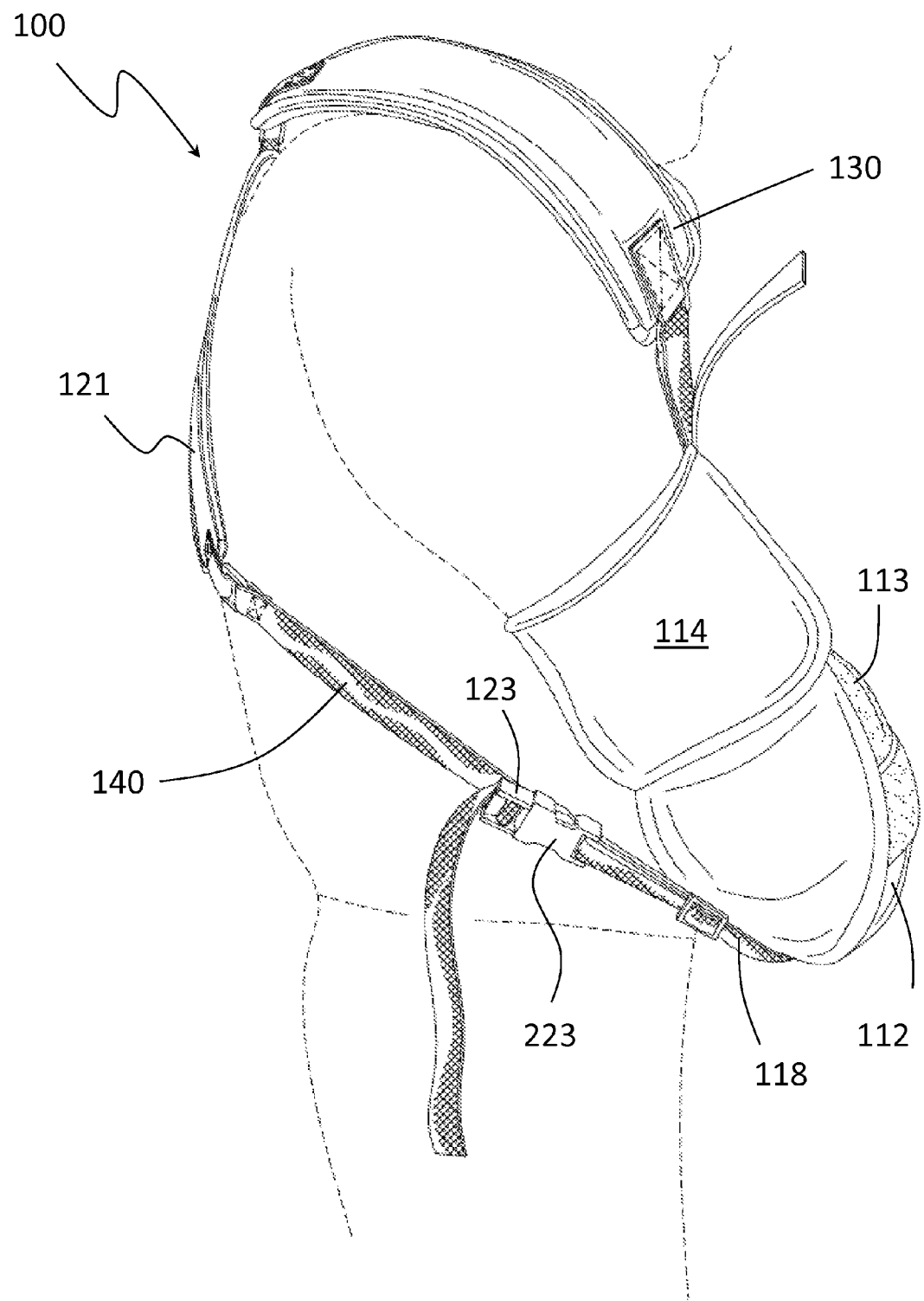
FIG. 3 shows a side perspective view of a limb support device with environment.

According to at least one exemplary embodiment, and referring to FIGS. 1-3 generally, a limb support device 100 may be disclosed. The device may include a sling 110 and a support harness 120. Support harness 120 may be configured to secure sling 110 to a user's body and disperse the weight of the limb to other areas of a user's body, such as a user's shoulders. Sling 110 may further include a lower section 112 and an upper section 114. Lower section 112 and upper section 114 may be shaped and sized to fit a limb, for example an arm, which may include a joint, for example an elbow. In such an embodiment, sling may be substantially L-shaped, lower section 112 may be shaped and sized to hold a forearm, and upper section 114 may be shaped and sized to fit an upper arm. In some exemplary embodiments, sling 110 may optionally be made of a pliable material capable of conforming to the shape of a limb, cast, or brace and also capable of supporting the limb, cast, or brace. Lower section 112 and upper section 114 may combine to form a substantially L-shaped sling 110. Sling 110 may further be capable of including additional padding or inserts to better support a limb, provide protection, or help maintain a desired form. In an exemplary embodiment, there may be an elbow pad insert within sling 110. The elbow pad insert may be sewn or otherwise secured within sling 110.

Lower section 112 and upper section 114 may also be of variable size, with fasteners 113, 116 to adjust the size, close the sling, or to allow a user to remove his or her limb from sling 110. Lower section 112 may form a U-shaped cross section when a limb is disposed in sling 110, and straps 117 may engage fasteners 113 to secure or close opposing edges 111. Fastener 116 may similarly secure or close opposing edges 115 of upper section 114 around the upper arm of a user. This may further facilitate the support of limbs in casts or braces. Fasteners described herein, including but not limited to fasteners 113, 116, may be for example, buckles, buttons, straps, hook-and-loop fasteners, or other types of fasteners as would be understood by a person having ordinary skill in the art. In an exemplary embodiment, fasteners 113 may be loop material of a hook-and-loop type fastener disposed over an area of the surface of sling 110. In an exemplary embodiment, fasteners 113 may be disposed on outer surfaces of lower section 112, including proximate edges 111. Straps 117 may have counterpart hook material disposed on at least a portion of an interior surface on each end opposite fasteners 222. This hook material may engage fasteners 113. In other exemplary embodiments, a first end of straps 117 may be sewn or otherwise affixed to lower section 112 proximate an edge 111. A second end of straps 117 may have hook material disposed on at least a portion of an interior surface thereof for engaging fasteners 113, which may be disposed on the outer surface of sling 110 proximate opposite edge 111 from where the first end of straps 117 are affixed.

Limb support device 100 may further include a support harness 120. Harness 120 may include a central back portion 121, at least one support strap 130 and at least one securing strap 140. In an exemplary embodiment, limb support device 100 may include two support straps 130 and two securing straps 140. Support straps 130 and securing straps 140 and central back portion 121 may be connected such that support straps 130 are capable of connecting to sling 110 and passing over a user's shoulders, where support straps 130 may then connect to central back portion 121. Central back portion 121 may rest against a user's back and the at least one securing strap 140 may connect to central back portion 121 and pass around a user's torso, under the user's arms, to connect to sling 110. Each strap from harness 120 may be capable of attaching to sling 110 by a fastener 122, 123. Through at least one support strap 130 and at least one securing strap 140, harness 120 may secure a sling 110 to a user's body and may support a limb disposed in the sling by transferring its weight to other parts of the user's body. Fasteners connecting harness 120 to sling 110 may allow a user to take on and off the device. The harness 120 may be configured to disperse the weight over multiple areas of a user's body, such as, but not limited to, a user's back and shoulders. Support straps 130 and securing straps 140 may be permanently or removably attached to the central back portion 121 of harness 120. Support straps 130 may include front fasteners 122 and securing straps 140 may include lower fasteners 123. Counterpart front fasteners 222 and counterpart lower fasteners 223 may be affixed to sling 110 or integrally formed in sling 110.

In some exemplary embodiments, counterpart fasteners 222, 223 may be affixed to spacing straps 117, 118, which may in turn be affixed to sling 110. In an exemplary embodiment, sling 110 may include two spacing straps 118. Each spacing strap 118 may be affixed to sling 110 on one end and may have a counterpart fastener 223 on the other, which may engage a fastener 123 affixed to a securing strap 140. In an exemplary embodiment, spacing straps 118 may be sewn to sling 110. A first spacing strap 118 or fastener 223 may be affixed to sling 110 proximate the intersection of lower section 112 and upper section 114. A second spacing strap 118 or fastener 223 may be affixed to sling 110 proximate the end of lower section 112 opposite the intersection with upper section 114. Each fastener 223 affixed to the end of a spacing strap 118 or affixed directly to sling 110 may be capable of engaging a fastener 123 disposed on the at least one securing strap 140. In some alternative embodiments, sling 110 may include one strap 118, which may pass through a channel running along the underside of sling 110 and strap 118 may have a counterpart fastener 223 at each end to engage fasteners 123 on the at least one securing strap 140. Fasteners 122, 123 and counterpart fasteners 222, 223 may optionally be coded to facilitate matching the fasteners to their intended counterparts. Coding may include color coding through the use of colored material, colored marks or dots, or through the addition of colored stickers. In an exemplary embodiment having two fasteners 122, two fasteners 123, two counterpart fasteners 222, and two counterpart fasteners 223, each of the four fasteners 122, 123 may be a different color and each of the four counterpart fasteners 222, 223 may match the color of the fastener 122, 123 it is intended to engage. Further, in embodiments where fasteners 122, 123 and counterpart fasteners 222, 223 are buckles, such as side release buckles, all fasteners affixed to harness 120 may be male and all fasteners affixed to sling 110 may be female. For exemplary purposes, in one embodiment, all fasteners, or buckles, affixed to sling 110 may be female and may be oriented by color as follows. A first counterpart fastener 222 may include blue color coding on a first side and red color coding on a reverse side. A second counterpart fastener 222 may include red color coding on a first side and blue color coding on a reverse side. The harness 120 may include four male buckles colored as follows. A first front male buckle 122 may be blue, a second front male buckle 122 may be red, a first lower male buckle 123 may be yellow, and a second lower male buckle 123 may be green. Counterpart fasteners 222, or buckles, may therefore have reverse color coding on opposite sides, while fasteners or buckles 122 may have the same color coding on both sides. This may allow sling 110 to be utilized in different orientations, such as on a left or right arm, and may facilitate matching fasteners. Lower sling buckles 223 may also optionally be colored yellow or green to match a counterpart, respectively.

In some exemplary embodiments, support straps 130 may include padding, which may be integrated in support straps 130 or may be affixed to support straps 130. Additionally, back portion 121 of harness 120 may include padding, as would be understood by a person having ordinary skill in the art. Padding may include different types of material, additional layers of material and/or ergonomic shaping, as would be understood by a person having ordinary skill in the art. Straps 117 may further serve to close bottom section 112 around a limb, cast or brace. Straps 117 may include a fastener, such as a hook-and-loop type fastener, which may engage a counterpart hook-and-loop portion 113 on lower section 112, as described above and as shown in exemplary FIG. 2. The fastener, such as a hook-and-loop type fastener disposed on strap 117 may extend for any desired length along a surface of strap 117. Straps and fasteners referenced throughout this description may be configured to be adjustable in length, as would be understood by a person having ordinary skill in the art. This may accommodate users of various sizes. It may also allow a user to adjust the weight disbursement and the orientation of the supported limb by adjusting the length of the series of straps.

In further exemplary embodiments, a pillow or grip-ball may be attached to sling 110. A pillow attachment or grip-ball may be beneficial for certain recovery processes, such as from Rotator Cuff Repair Surgery, as would be understood by a person having ordinary skill in the art. A grip-ball or pillow may be attached to sling 110 by securing to fastener 113, which may include loop material of a hook-and-loop type fastener disposed on the outer surface of sling 110. Additionally, in some embodiments, limb support device 100 may include color accents. Color accents may be used to identify a size. Color accents may be used on the borders or binding of sling 110 for this purpose. For exemplary, non-limiting, purposes, a red border may indicate large, a blue border may indicate medium, and a green border may indicate small.

In some alternative embodiments, limb support device may include a sling, a securing strap, and one or more support straps. Securing strap may be affixed to a lower section of the sling and may be capable of wrapping around a wearer's body. Support straps may also be affixed to a lower section of the sling and may be capable of passing over a wearer's shoulders and securing to securing strap on the back side of the wearer. Support straps may disperse the weight of the limb to the wearer's shoulders. The size of the securing strap around a user's body, for example the user's torso, may be adjustable through the use of fasteners and adjustable buckles. Fasteners may include, buttons or hook-and-loop fasteners, or other types of fasteners as would be understood by a person having ordinary skill in the art. Fasteners and buckles may also provide for opening the limb support device and placing on or removing from a user.

Support straps may hold and support a limb support device upon a user's body, for example by going over a user's shoulders. Each support strap may further include a buckle and fastener. A fastener may be for example, buttons or hook-and-loop fasteners, or as desired. The buckle and fastener may together provide for adjusting the size of support straps around a user's body. The buckle and fastener may also provide for opening a limb support device and placing on or removing from a user.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A limb support device comprising:
    a sling having an upper section and a lower section, the upper and lower sections of the sling being configured to hold a limb; and
    a support harness configured to disperse weight from the sling, the support harness having a central back portion, two securing straps, and two support straps;
    wherein the central back portion comprises a top portion, a first bottom portion and a second bottom portion;
    wherein the two securing straps each releasably couple to a respective one of the first bottom portion and the second bottom portion of the central back portion with a fastener and include a lower fastener for connecting to a counterpart lower fastener disposed on the sling; and
    wherein each of the two support straps releasably couple to the top portion of the central back portion with a fastener and include a front fastener for connecting to a counterpart front fastener disposed on the sling;
    further comprising spacing straps configured to connect each counterpart front fastener and each counterpart lower fastener to the sling.

2. The limb support device of claim 1, wherein the spacing straps are configured to connect each counterpart front fastener to the sling are further configured to removably secure the lower section of the sling around the limb.

3. The limb support device of claim 1, wherein the sling comprises a pliable material.

4. The limb support device of claim 1, further comprising at least one fastener disposed on the upper section of the sling configured to enclose the sling around the limb and at least one fastener disposed on the lower section of the sling to enclose the sling around the limb, and a pad disposed on an interior portion of the sling proximate the upper portion.

5. The limb support device of claim 1, further comprising padding on the two support straps and wherein the fasteners that releasably couple the two support straps to the central back portion facilitate adjusting fitment of the sling holding the limb.

6. The limb support device of claim 1, further comprising padding on the central back portion.

7. The limb support device of claim 1, wherein the length of the two securing straps and the two support straps is adjustable with respect to the sling and the central back portion.

8. The limb support device of claim 1, further comprising color accents indicating a size.

9. A limb support device comprising:
    a sling having an upper section and a lower section, the upper and lower sections of the sling being configured to hold a limb; and
    a support harness configured to disperse weight from the sling, the support harness having a central back portion, two securing straps, and two support straps;
    wherein the central back portion comprises a top portion, a first bottom portion and a second bottom portion;
    wherein the two securing straps each releasably couple to a respective one of the first bottom portion and the second bottom portion of the central back portion and include a lower fastener for connecting to a counterpart lower fastener disposed on the sling; and
    wherein each of the two support straps releasably couple to the top portion of the central back portion and include a front fastener for connecting to a counterpart front fastener disposed on the sling;
    further comprising at least one fastener disposed on the upper section of the sling configured to enclose the sling around the limb and at least one fastener disposed on the lower section of the sling to enclose the sling around the limb.

10. The limb support device of claim 9, further comprising spacing straps configured to connect each counterpart front fastener and each counterpart lower fastener to the sling.

11. The limb support device of claim 10, wherein the spacing straps are configured to connect each counterpart front fastener to the sling are further configured to removably secure the lower section of the sling around the limb.

12. The limb support device of claim 9, wherein the sling comprises a pliable material.

13. The limb support device of claim 9, further comprising padding on the two support straps.

14. The limb support device of claim 9, further comprising padding on the central back portion.

15. The limb support device of claim 9, wherein the length of the two securing straps and the two support straps is adjustable with respect to the sling and the central back portion.

16. The limb support device of claim 9, further comprising color accents indicating a size.

* * * * *